United States Patent [19]

Ishizuka et al.

[11] Patent Number: 5,008,462

[45] Date of Patent: Apr. 16, 1991

[54] METHOD FOR PREPARING MONOCHLOROACETALDEHYDE TRIMER

[75] Inventors: Makoto Ishizuka, Kawaguchi; Takashi Wakasugi, Iwaki both of Japan

[73] Assignee: Kureha Chemical Industry Co., Ltd., Tokyo, Japan

[21] Appl. No.: 433,284

[22] Filed: Nov. 8, 1989

[30] Foreign Application Priority Data

Nov. 9, 1988 [JP] Japan .................. 63-282980

[51] Int. Cl.$^5$ .............. C07C 45/61; C07C 45/63
[52] U.S. Cl. .................. 568/466; 568/449; 568/458; 568/488; 568/490; 568/495
[58] Field of Search ............... 568/458, 466, 488, 490, 568/491, 492, 495, 449

[56] References Cited

U.S. PATENT DOCUMENTS 4,311,563  1/1982  Opavsky et al. ............... 568/492
4,579,976  4/1986  Cheminal et al. ............... 568/490

FOREIGN PATENT DOCUMENTS 623772  7/1961  Canada ........................... 568/488
635789  4/1950  United Kingdom ............ 568/488

*Primary Examiner*—Werren B. Lone
*Attorney, Agent, or Firm*—Cushman, Darby & Cushman

[57] ABSTRACT

A method for preparing a monochloroacetaldehyde trimer in a high yield is here disclosed which comprises the steps of dissolving, in an organic solvent, a solution containing monochloroacetaldehyde as the main component, and then trimerizing monochloroacetaldehyde in the presence of sulfuric acid. The thus prepared monochloroacetaldehyde trimer can be heated at 120° C. under atmospheric pressure to obtain pure monochloroacetaldehyde.

13 Claims, No Drawings

METHOD FOR PREPARING MONOCHLOROACETALDEHYDE TRIMER

BACKGROUND OF THE INVENTION

1. Field of the Invention

The present invention relates to an improved method for preparing a high-purity monochloroacetaldehyde trimer.

2. Description of the Prior Art

Monochloroacetaldehyde which is useful as a raw material for the synthesis of medicines and agricultural chemicals is manufactured by a known method, i.e., by chlorinating acetaldehyde, para-acetaldehyde or vinyl acetate.

However, monochloroacetaldehyde is very unstable and is extremely liable to polymerize itself. For this reason, it is impossible to preserve monochloroacetaldehyde for a long period of time, and therefore, nowadays, this compound is kept in the state of an aqueous solution (Japanese Patent Laid-open No. 99336/1987).

However, monochloroacetaldehyde tends to bring about condensation polymerization even in the aqueous solution in order to develop a color. This fact impedes the preparation of high-quality monochloroacetaldehyde which is required in recent years.

An attempt has been made to form a trimer of monochloroacetaldehyde with the intention of preparing high-purity monochloroacetaldehyde which can be stored for a long term, by Natterer [Monatsh, 3, 461-464 (1882)]. In this attempt, the trimer of monochloroacetaldehyde is formed by shaking, together with concentrated sulfuric acid, high-purity monochloroacetaldehyde obtained by the reaction between monochloroacetal and oxalic anhydride, the volume of concentrated sulfuric acid being one half of that of monochloroacetaldehyde. When the thus formed trimer is heated, decomposition occurs to obtain pure monochloroacetaldehyde. However, in this report, any actual yield and any identification of a structure are not elucidated.

In the method suggested by Natterer, expensive monochloroacetal and oxalic anhydride are necessary to obtain pure monochloroacetaldehyde. In addition, according to experiments by inventors of the present application, the Natterer's method has the following disadvantages: In the direct reaction between monochloroacetaldehyde and concentrated sulfuric acid, operation is very difficult, and a great deal of black tar-like substance is formed. As a result, the yield of the desired monochloroacetaldehyde trimer is as low as about 20% disadvantageously.

SUMMARY OF THE INVENTION

In view of the above-mentioned situations, the present invention has been achieved. That is, an object of the present invention is to provide a method for preparing a high-purity monochloroacetaldehyde trimer in a high yield.

The other objects and features of the present invention will be apparent from the following description.

The feature of the present invention resides in that a reaction solution containing, as the main component, monochloroacetaldehyde obtained by chlorinating acetaldehyde, para-acetaldehyde or vinyl acetate is dissolved in an organic solvent, and the reaction solution is then trimerized in the presence of sulfuric acid.

That is, in the present invention, concentrated sulfuric acid is reacted with monochloroacetaldehyde easily obtained by chlorinating inexpensive para-acetaldehyde or acetaldehyde in the presence of an organic solvent such as hexane, and therefore the high-purity monochloroacetaldehyde trimer can be prepared in a high yield advantageously.

DETAILED DESCRIPTION OF THE INVENTION

In the present invention, a solution containing monochloroacetaldehyde as the main component which can be used to trimerize monochloroacetaldehyde has the composition comprising 70% by weight or more of monochloroacetaldehyde, 8% by weight or less of dichloroacetaldehyde, 12% by weight or less of acetaldehyde, 5% or less of high-boiling components and 5% by weight or less of hydrogen chloride.

The solution having such a composition can be obtained by chlorinating acetaldehyde, para-acetaldehyde, vinyl acetate or the like. This chlorinated solution preferably has a chlorination degree of 0.5 to 0.9 so as to inhibit the secondary production of dichloroacetaldehyde. The latter forms a crystalline copolymer together with monochloroacetaldehyde, and thus dichloroacetaldehyde lowers the yield and purity of the desired monochloroacetaldehyde trimer inconveniently.

The composition of the reaction solution obtained by the chlorination can be adjusted by changing a reaction time and a temperature. Moreover, after completion of the chlorination reaction, an inert gas such as a nitrogen gas is then blown into the reaction solution, or alternatively the latter is subjected to distillation in order to remove an unreacted chlorine gas, hydrogen chloride, low-boiling and high-boiling components therefrom, whereby the reaction solution which contains monochloroacetaldehyde at a high concentration can be prepared.

In the present invention, the raw material solution containing the above-mentioned monochloroacetaldehyde as the main component is dissolved in an organic solvent, and the resulting reaction solution is then reacted with concentrated sulfuric acid at a temperature of 0° C. or less, preferably −5° C. or less to prepare a monochloroacetaldehyde trimer. In this reaction, the amount of concentrated sulfuric acid which is added as the catalyst is from 10 to 70% by weight, preferably 15 to 60% by weight with respect to the weight of the raw material solution If the amount of concentrated sulfuric acid is less than 10% by weight, the trimerization reaction for monochloroacetaldehyde does not make progress sufficiently, and inversely if it is more than 70% by weight, the high-boiling components are produced in large quantities, with the result that the yield of the monochloroacetaldehyde trimer deteriorates.

Examples of the organic solvent used in the present invention include aliphatic hydrocarbons having 5 to 10 carbon atoms such as hexane, heptane and cyclohexane; aromatic hydrocarbons having 9 or less carbon atoms such as benzene, toluene and xylene; petroleum ether, carbon tetrachloride and carbon disulfide. In addition, acetonitrile, an alcohol such as ethanol, an ester such as ethyl acetate, and ethers such as diethyl ether and tetrahydrofuran can also be used as the organic solvent. The amount of the organic solvent is 1 to 20 times, preferable 2 to 10 times as much as that of the raw material. When the raw material is diluted with the organic solvent, monochloroacetaldehyde is uniformly brought into contact with concentrated sulfuric acid, so that the secondary production of high-boiling components is inhibited and hence the high-purity monochloroacetaldehyde trimer is prepared in a high yield.

By the above-mentioned reaction, the trimer of monochloroacetaldehyde is deposited in the form of crystals. After completion of the reaction, the formed monochloroacetaldehyde trimer is then separated. The preferable procedure of this separation is as follows: The above-mentioned kind of organic solvent, preferably the same kind of organic solvent as used previously and water are added to the reaction solution, followed by heating to dissolve the crystals therein. The resulting organic layer is then separated and washed with water under heating. Preferably, the organic layer is further washed with an aqueous sodium hydroxide solution and water. Afterward, the thus washed organic layer is dried with magnesium sulfate or the like and then cooled to deposit the desired monochloroacetaldehyde trimer in the form of crystals, and the deposited crystals are separated from the solution. In this case, the amount of the organic solvent which is added to the reaction solution is such that the crystals are dissolved at a temperature lower than the boiling point of the organic solvent, and the amount of water which is added to the reaction solution is such that the concentration of sulfuric acid is 30% or less, preferably 15% or less.

Furthermore, the formed monochloroacetaldehyde trimer may be separated from the reaction solution by another preferable procedure: Ether such as diethyl ether is added to the reaction solution so as to dissolve the crystals, and the resulting organic layer is then washed with water, preferably with an aqueous sodium hydroxide solution and water. Afterward, the thus washed organic layer is dried with magnesium sulfate or the like, and ether is then distilled off. Afterward, the deposited crystals of the monochloroacetaldehyde trimer are separated from the solution. According to the above-mentioned procedure, the monochloroacetaldehyde trimer can be prepared in a purity of 95% or more, but if purification is additionally carried out by recrystallization from a solvent such as hexane, the desired product having a purity of 99% or more can be prepared in the form of crystals.

Now, the present invention and its effect will be described in detail in reference to examples and comparative examples, but the scope of the present case should not be limited only to these examples.

EXAMPLE 1

In a 1-liter three-necked flask equipped with a stirrer, a reflex condenser and a thermometer were placed 500 g of para-acetaldehyde and 5 ml of water, and the temperature of the solution was maintained at 10° C. A chlorine gas was then blown through the solution at a flow rate of 0.15 liter/minute in order to start reaction. Afterward, while the reaction temperature was gradually adjusted to 2±1° C., the chlorine gas was blown therethrough at a flow rate of 0.15 to 0.80 liter/minute over 5 hours in order to perform chlorination. At this time, a generated hydrogen chloride gas was guided to an aqueous sodium hydroxide solution.

Afterward, a nitrogen gas was blown through the reaction liquid mixture (about 900 g) for 30 minutes in order to remove an unreacted chlorine gas and low-boiling components therefrom and to concentrate monochloroacetaldehyde.

The thus prepared reaction solution was analyzed by the use of gas chromatography. As a result, it was confirmed that the reaction solution was composed of 10.5% by weight of acetaldehyde, 76.4% by weight of monochloroacetaldehyde, 6.5% by weight of dichloroacetaldehyde and trace amounts of hydrogen chloride and high-boiling components.

The preparation of a trimer from this reaction solution was carried out in a 1-liter three-necked flask equipped with a stirrer and a thermometer. In the flask, 64.4 g (50 ml) of the reaction solution having the above-mentioned composition was added to 200 ml of hexane and then cooled down to −20° C. Afterward, 7.5 ml (21% by weight based on the weight of the reaction solution) of 96% concentrated sulfuric acid was gradually added to the solution over 20 minutes. While the temperature of the solution was maintained at −10° C. or less, stirring was then continued for 1 hour in order to form fine crystals. After completion of the reaction, 500 ml of diethyl ether was added thereto so as to dissolve the crystals. The resulting organic layer was washed with water and a 10% aqueous sodium hydroxide solution, and then dried with magnesium sulfate. Afterward, the used solvent was removed therefrom under reduced pressure (20 mmHg). The resulting crude crystals were recrystallized from 500 ml of hexane, so that 25.7 g of a monochloroacetaldehyde trimer having a purity of 100% was prepared in the state of white needle crystals. The yield of the thus prepared monochloroacetaldehyde trimer was 52.2% based on the weight of monochloroacetaldehyde present in the reaction solution.

It was confirmed on the basis of m.p., GC-MS, IR, elemental analysis and NMR that the prepared monochloroacetaldehyde trimer had the structure in which a six-membered ring was formed by 3 molecules of monochloroacetaldehyde.

Analytical values of the product were as follows:

m.p.: 87°–88° C.
Molecular weight: 235.5
IR: 1130 cm$^{-1}$ (C—O stretching)
Elemental analysis:
Calcd. C 30.60%; H 3.85%; Cl 45.16%,
Found C 30.53%; H 3.71%; Cl 44.79%,
NMR: 3.5 ppm (6H, d, CH$_2$),
5 5.1 ppm (3H, t, CH),

EXAMPLE 2

Under the same chlorination conditions as in Example 1 with the exception that para-acetaldehyde was replaced with acetaldehyde, chlorination was carried out. About 20% by weight of butyl chloral which was formed in the chlorination step was then removed by distillation under atmospheric pressure, and afterward, the chloral-free solution was used as a raw material reaction solution.

The thus obtained reaction solution was analyzed, and it was confirmed that the reaction solution was composed of 8.7% by weight of acetaldehyde, 75.5% by weight of monochloroacetaldehyde, 4.0% by weight of dichloroacetaldehyde and trace amounts of hydrogen chloride and high-boiling components.

The trimerization reaction was performed by reacting 39.6 g (30 ml) of the reaction solution having the above-mentioned composition with 9 ml (42% by weight based on the weight of the reaction solution) of concentrated sulfuric acid in accordance with the same procedure as in Example 1.

As a result, 20.0 g of white needle crystals containing 95.5% by weight of a monochloroacetaldehyde trimer was prepared. The yield of the thus prepared monochloroacetaldehyde trimer was 63.9%.

COMPARATIVE EXAMPLE 1

In a 250-milliliter eggplant type flask were placed 82.3 g of monochloroacetal and 48.7 g of oxalic anhydride, and distillation was then carried out at a bath temperature of 110° C. under atmospheric pressure.

After the distillation had been carried out twice, 37.9 g of the resulting distillate was analyzed by gas chromatography. As a result, it was confirmed that the distillate contained 85.7% by weight of monochloroacetaldehyde.

Into a 100-milliliter test tube was poured 37.1 g (30 ml) of this distillate, and it was cooled to −30° C. Afterward, 15 ml of concentrated sulfuric acid was gradually added thereto with shaking.

The reaction mixture was allowed to stand for 4 hours, while temperature was maintained at −30° C. or less, in order to obtain crude crystals. The latter were then washed with a 10% aqueous sodium hydroxide solution and a small amount of cooled ethyl alcohol.

Afterward, recrystallization was carried out by the use of 100 ml of ethyl alcohol to prepare 6.51 g of white needle crystals.

The yield of the prepared monochloroacetaldehyde trimer was as low as 20.5%.

EXAMPLE 3

The same procedure as in Example 1 was repeated with the exception that hexane used as the solvent in Example 1 was replaced with each of solvents shown in the following table, in order to prepare a monochloroacetaldehyde trimer.

Yields of the prepared monochloroacetaldehyde trimer are also set forth in the following table.

TABLE

| Solvent | Yield of Monochloroacetaldehyde Trimer (%) |
| --- | --- |
| Cyclohexane | 44.1 |
| Heptane | 41.0 |
| Petroleum ether | 36.0 |
| Benzene | 49.3 |
| Toluene | 45.2 |
| Carbon tetrachloride | 53.6 |
| Carbon disulfide | 47.5 |

EXAMPLE 4

In a 3-liter three-necked flask equipped with a stirrer, a reflex condenser and a thermometer were placed 994 g of para-acetaldehyde and 9 ml of water, the temperature of the solution was maintained at 10° C. A chlorine gas was then blown through the solution at a flow rate of 0.15 liter/minute in order to start reaction. Afterward, while the reaction temperature was gradually adjusted to 2±1° C., the chlorine gas was blown therethrough at a flow rate of 0.15 to 0.80 liter/minute over 6 hours in order to perform chlorination. At this time, a generated hydrogen chloride gas was guided to an aqueous sodium hydroxide solution.

The thus chlorinated solution was analyzed by the use of gas chromatography. As a result, it was confirmed that the reaction solution was composed of 17.41% by weight of acetaldehyde, 47.88% by weight of monochloroacetaldehyde, 5.29% by weight of dichloroacetaldehyde and trace amounts of hydrogen chloride and high-boiling components. In this case, a chlorination degree was 0.828.

Next, this reaction solution (about 1,920 g) was distilled under reduced pressure to remove low-boiling and high-boiling components therefrom and to concentrate monochloroacetaldehyde. The resulting distillate (639.8 g) obtained at a boiling point of 95° C./150 mmHg was used as a raw material for preparation of a trimer.

The distillate was analyzed through the gas chromatography, so as to confirm that the distillate was composed of 84.05% by weight of monochloroacetaldehyde, 5.67% by weight of dichloroacetaldehyde and a trace amount of high-boiling components.

The preparation of the trimer from this chlorinated solution was carried out in a 3-liter three-necked flask equipped with a stirrer and a thermometer. In the flask, 371.3 g of the chlorinated solution having the above-mentioned composition was dissolved into 1,200 ml of hexane and then cooled to −5° C. Afterward, 52 ml (26% by weight based on the weight of the reaction solution) of 96% concentrated sulfuric acid was gradually added to the solution over 30 minutes. While the temperature of the solution was maintained at −5° C. or less, stirring was then continued for 3 hours in order to obtain fine crystals.

After completion of the reaction, 1,650 ml of hexane and 500 ml of water were added thereto, and the mixture was then heated to 60° C. in order to dissolve the crystals in hexane. The resulting sulfuric acid layer was removed, and the organic layer was then washed repeatedly with a 10% aqueous sodium hydroxide solution and water.

The thus treated solution was allowed to stand at room temperature, thereby obtaining 201.2 g of the desired monochloroacetaldehyde trimer having a purity of 95.6% in the form of white needle crystals.

The thus obtained crystals were collected by filtration and then recrystallized from 2,900 ml of hexane in order to prepare 166.2 g of the monochloroacetaldehyde trimer having a purity of 99.5% in the form of columnar crystals. The yield of the prepared monochloroacetaldehyde trimer was 53.0% based on the content of monochloroacetaldehyde in the chlorinated solution used in the trimerization reaction.

The results of the above-mentioned examples and comparative examples indicate that the method for preparing the monochloroacetaldehyde trimer of the present invention is excellent and industrially useful.

What is claimed is:

1. A method of preparing a monochloroacetaldehyde trimer comprising:
   (a) dissolving a raw material solution in an organic solvent, wherein said raw material solution contains at least 70% by weight monochloroacetaldehyde;
   (b) cooling the solution to a temperature of 0° C. or less; and
   (c) reacting the solution with concentrated sulfuric acid in an amount of 10 to 70% by weight with respect to the weight of the raw material solution.

2. The method for preparing a monochloroacetaldehyde trimer according to claim 1 wherein said raw material solution containing monochloroacetaldehyde in an amount of at least 70% by weight is a reaction solution obtained by chlorinating a compound selected from acetaldehyde and para-acetaldehyde.

3. The method for preparing a monochloroacetaldehyde trimer according to claim 2 wherein said chlorination is carried out so that the chlorination degree of said reaction solution to be in a range of from 0.5 to 0.9.

4. The method for preparing a monochloroacetaldehyde trimer according to claim 2 wherein said reaction solution is composed of 70% by weight or more of monochloroacetaldehyde, 8% by weight or less of dichloroacetaldehyde, 12% by weight or less of acetaldehyde, 5% by weight or less of high-boiling components and 5% by weight or less of hydrogen chloride.

5. The method for preparing a monochloroacetaldehyde trimer according to claim 1 wherein the amount of sulfuric acid is from 15 to 60% by weight based on the weight of said solution containing monochloroacetaldehyde as the main component.

6. The method for preparing a monochloroacetaldehyde trimer according to claim 1 wherein said trimerization is carried out at a temperature of $-5°$ C. or less.

7. The method for preparing a monochloroacetaldehyde trimer according to claim 1 wherein said organic solvent is selected from the group consisting of hexane, cyclohexane, heptane, benzene, toluene, carbon tetrachloride and carbon disulfide.

8. The method for preparing a monochloroacetaldehyde trimer according to claim 1 further containing the step of separating, from said reaction solution, the deposited crystals of said monochloroacetaldehyde trimer obtained by trimerizing monochloroacetaldehyde.

9. The method for preparing a monochloroacetaldehyde trimer according to claim 8 wherein said separation of said monochloroacetaldehyde trimer crystals from said reaction solution is carried out by first adding an organic solvent and water to said reaction solution after completion of said reaction in order to dissolve said crystals therein, then separating the resulting organic layer therefrom, washing said organic layer with water under heating or with an aqueous sodium hydroxide solution and water, drying said washed organic layer with a drying agent, cooling the same to deposit crystals, and separating said crystals therefrom.

10. The method for preparing a monochloroacetaldehyde trimer according to claim 9 wherein said organic solvent is the same as used in said trimerization reaction of monochloroacetaldehyde.

11. The method for preparing a monochloroacetaldehyde trimer according to claim 8 wherein said separation of said monochloroacetaldehyde trimer crystals from said reaction solution is carried out by adding ether to said reaction solution after completion of said reaction in order to dissolve said crystals therein, then washing the resulting organic layer with water or with an aqueous sodium hydroxide solution and water, drying said washed organic layer with magnesium sulfate, distilling off ether, and separating deposited crystals therefrom.

12. A method of preparing a monochloroacetaldehyde trimer comprising:
   (a) preparing a raw material solution of at least 70% by weight monochloroacetaldehyde by chlorinating a compound selected from acetaldehyde and para-acetaldehyde.
   (b) dissolving said raw material solution in an organic solvent;
   (c) cooling the solution to a temperature of 0° C. or less;
   (d) reacting the solution with concentrated sulfuric acid in an amount of 10 to 70% by weight with respect to the weight of the raw material solution; and
   (e) separating the deposited crystals of the monochloroacetaldehyde trimer from the organic solution.

13. A method of preparing a monochloroacetaldehyde trimer as claimed in claim 9, wherein the drying agent is magnesium sulfate.

* * * * *